(12) United States Patent
Inoue

(10) Patent No.: US 10,307,419 B2
(45) Date of Patent: Jun. 4, 2019

(54) TABLET COMPRISING 7-[4-(4-BENZO[B]THIOPEN-4-YL-PIPERAZIN-1-YL)BUTOXY]-1H-QUINOLIN-2-ONE OR A SALT THEREOF

(71) Applicant: OTSUKA PHARMACEUTICAL CO., LTD., Tokyo (JP)

(72) Inventor: Yoshiharu Inoue, Osaka (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 15/713,427

(22) Filed: Sep. 22, 2017

(65) Prior Publication Data

US 2018/0008600 A1    Jan. 11, 2018

Related U.S. Application Data

(63) Continuation of application No. 15/444,113, filed on Feb. 27, 2017, now abandoned, which is a continuation of application No. 15/019,874, filed on Feb. 9, 2016, now abandoned, which is a continuation of application No. 14/351,325, filed as application No. PCT/JP2012/076415 on Oct. 12, 2012, now abandoned.

(30) Foreign Application Priority Data

Oct. 14, 2011    (JP) .................................. 2011-227057

(51) Int. Cl.
    A61K 31/496    (2006.01)
    A61K 9/20      (2006.01)
    A61K 9/28      (2006.01)
    A61K 9/00      (2006.01)

(52) U.S. Cl.
    CPC .......... *A61K 31/496* (2013.01); *A61K 9/0056* (2013.01); *A61K 9/205* (2013.01); *A61K 9/2013* (2013.01); *A61K 9/2018* (2013.01); *A61K 9/2054* (2013.01); *A61K 9/2059* (2013.01); *A61K 9/2813* (2013.01); *A61K 9/2866* (2013.01)

(58) Field of Classification Search
    None
    See application file for complete search history.

(56) References Cited

U.S. PATENT DOCUMENTS

| 6,562,375 | B1 | 5/2003 | Sako et al. |
| 7,888,362 | B2 | 2/2011 | Yamashita et al. |
| 2003/0153617 | A1* | 8/2003 | Dalen ................. A61K 9/2866 514/460 |
| 2005/0043325 | A1 | 2/2005 | Bell et al. |
| 2007/0154544 | A1 | 7/2007 | Hrakovsky et al. |
| 2008/0187582 | A1 | 8/2008 | Guitard et al. |
| 2009/0318560 | A1 | 12/2009 | Parent et al. |
| 2010/0105710 | A1 | 4/2010 | Murakawa et al. |
| 2010/0130569 | A1* | 5/2010 | Okamoto ............. A61K 31/428 514/367 |
| 2010/0179322 | A1 | 7/2010 | Yamashita et al. |
| 2011/0152286 | A1 | 6/2011 | Yamashita et al. |

FOREIGN PATENT DOCUMENTS

| ES | 2318693 T3 | 5/2009 |
| JP | 2006-61067 A | 3/2006 |
| JP | 2006-316052 | 11/2006 |
| JP | 2008-115172 | 5/2008 |
| JP | 2010-268748 A | 12/2010 |
| KR | 10-2010-0099113 | 9/2010 |
| WO | WO 2009/047565 A2 | 4/2009 |
| WO | WO 2012/137071 A1 | 10/2012 |

OTHER PUBLICATIONS

Abilify—FDA label, 2008.
Abilify—FDA label, Feb. 2011.
Communication pursuant to Rule 114(2) EPC dated Oct. 2, 2015, issued in European Patent Application No. 12840025.6.
Communication pursuant to Rule 94(3) EPC dated Dec. 11, 2015, issued in European Patent Application No. 12840025.6.
English-language International Search Report from the Japanese Patent Office for International Application No. PCT/JP2012/076415, dated Jan. 8, 2013.
Japanese Pharmaceutical Excipients Directory, Jul. 2007, pp. 66, 93, 181 and 223.
Maeda, Kenji, "Preclinical Pharmacology of Brexpiprazole (OPC-34712): A Novel Compound with Dopamine D2 Receptor Partial Agonist Activity," Sep. 2011.
Maeda et al., "Brexpiprazole I: In Vitro and In Vivo Characterization of a Novel Serotonin-Dopamine Activity Modulator," The Journal of Pharmacology and Experimental Therapeutics, 350: pp. 589-604m Sep. 2014.
Office Action dated Dec. 10, 2015 for EA Application No. 201490783.
Office Action for corresponding JP Application No. 2013-538582 dated Jul. 7, 2016.
"Otsuka HD places top priority on development of OPC-34712," Pharma Japan, 2219, 3 (Jan. 3, 2011).

(Continued)

*Primary Examiner* — Jeffrey T. Palenik
(74) *Attorney, Agent, or Firm* — Finnegan, Henderson, Farabow, Garrett & Dunner, LLP

(57) ABSTRACT

This invention relates to a tablet containing, as an active ingredient, 7-[4-(4-benzo[b]thiophen-4-yl-piperazin-1-yl)butoxy]-1H-quinolin-2-one or a salt thereof, that has excellent disintegration ability, storage stability and photostability.
The tablet of the present invention comprising an uncoated tablet containing 7-[4-(4-benzo[b]thiophen-4-yl-piperazin-1-yl)butoxy]-1H-quinolin-2-one or a salt thereof as an active ingredient, excipients such as lactose, corn starch, and microcrystalline cellulose; disintegrants such as low-substituted hydroxypropylcellulose, croscarmellose sodium, and sodium carboxymethyl starch; binders such as hydroxypropylcellulose; lubricants such as stearate;
and further comprising a coating layer, containing hypromellose; talc; titanium oxide; colorant; and the like, the coating layer being applied to the surface of the uncoated tablet.

7 Claims, 1 Drawing Sheet

(56) References Cited

OTHER PUBLICATIONS

Rowe, R.C., "The opacity of tablet film coatings," Journal of Pharmacy and Pharmacology, vol. 36, Jan. 1, 1984, pp. 569-572.
Strategy and Novel Technology on Pharmaceutical Preparations, Mar. 2007, pp. 30-31.
Supplementary European Search Report for corresponding EP Application No. EP 12 84 0025 dated Feb. 10, 2015.
Tiefenbacher, Eva-Maria et al., "Photodegradation of Some Quinolones Used as Antimicrobial Therapeutics," Journal of Pharmaceutical Sciences, Apr. 1994, vol. 83, No. 4, pp. 463-467.
Principles and equipment for coating of pharmaceutical preparations, 2006, pp. 123 to 125.
Decision of Rejection dated Jan. 6, 2017 in China Patent Application No. 201280050586.1.
Office Action for corresponding JP Application No. 2017-008854 dated Jan. 30, 2018.
Pharmaceutics: The Science of Dosage Form Design, 1988, $1^{st}$ Edition, pp. 134, 136, 249, 250, 303, 443 and 444.
Pharmaceutics: The Science of Dosage Form Design, 2002, $2^{nd}$ Edition, pp. 134, 136, 249, 250,303, 443 and 444.
Pharmaceutics: The Science of Dosage Form Design, 2002, 2nd Edition, p. 441.
Korean Office Action dated Jan. 3, 2019, issued in corresponding Korean Application No. 10-2014-7010656 by the Korean Intellectual Property Office.

\* cited by examiner

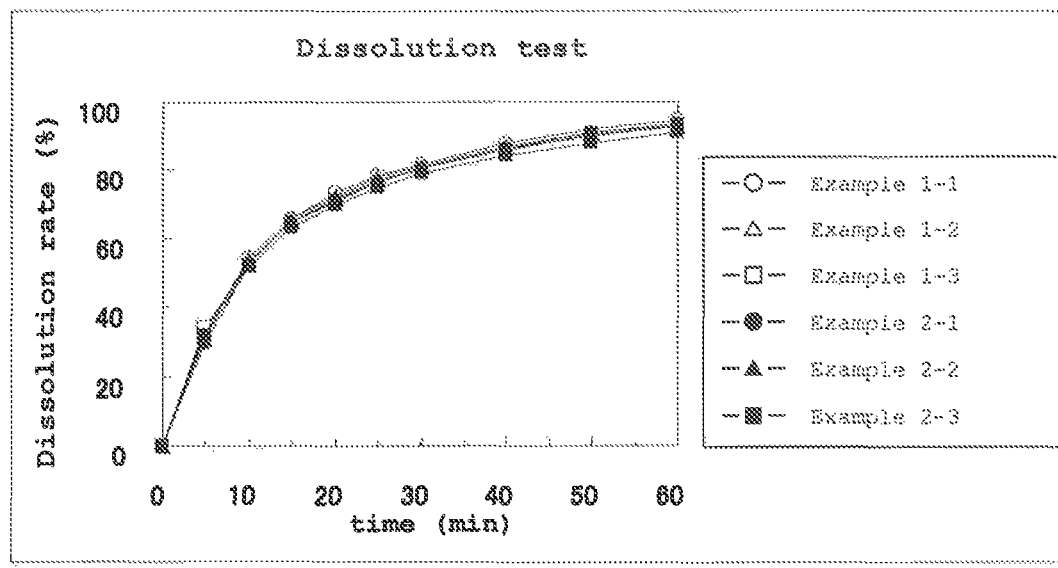

TABLET COMPRISING 7-[4-(4-BENZO[B]THIOPEN-4-YL-PIPERAZIN-1-YL)BUTOXY]-1H-QUINOLIN-2-ONE OR A SALT THEREOF

This application is a continuation of U.S. application Ser. No. 15/019,874, filed Feb. 9, 2016, which is a continuation of U.S. application Ser. No. 14/351,325, 371 (c) date of Apr. 11, 2014, now abandoned, which is the National Stage Application of PCT/JP2012/076415, filed Oct. 12, 2012, and claims benefit to JP 2011-227057 filed Oct. 14, 2011, all of which are incorporated herein by reference.

TECHNICAL FIELD

The present invention relates to a tablet comprising 7-[4-(4-benzo[b]thiophen-4-yl-piperazin-1-yl)butoxy]-1H-quinolin-2-one or a salt thereof as an active ingredient.

BACKGROUND ART

7-[4-(4-Benzo[b]thiophen-4-yl-piperazin-1-yl)butoxy]-1H-quinolin-2-one (hereunder referred to as Compound (I)) or a salt thereof is known to act as a dopamine $D_2$ receptor partial agonist, a serotonin 5-$HT_{2A}$ receptor antagonist, and an $\alpha_1$ adrenergic receptor antagonist, as well as a serotonin uptake inhibitor (or a serotonin reuptake inhibitor) (Patent Literature 1), and to possess a wide therapeutic spectrum in the treatment of central nervous system diseases (in particular, schizophrenia).

CITATION LIST

Patent Literature

PTL 1: Japanese Unexamined Patent Publication No. 2006-316052

SUMMARY OF INVENTION

Technical Problem

An object of the present invention is to provide a tablet comprising Compound (I) or a salt thereof as an active ingredient and having excellent disintegration ability, storage stability, and high photostability.

Solution to Problem

The present inventors conducted intensive research to achieve the above object and found that a tablet comprising Compound (I) or a salt thereof as an active ingredient and further comprising lactose, corn starch, microcrystalline cellulose or like excipient; low-substituted hydroxypropyl cellulose, croscarmellose sodium, sodium carboxymethyl starch or like disintegrant; and hydroxypropyl cellulose or like binder exhibits excellent disintegration ability and storage stability. The present inventors further found that higher photostability can be attained by applying a coating layer containing a colorant. The present invention was completed through further studies based on this finding, and provides the following items.

Item 1. A tablet comprising 7-[4-(4-benzo[b]thiophen-4-yl-piperazin-1-yl)butoxy]-1H-quinolin-2one or a salt thereof as an active ingredient.

Item 2. The tablet according to Item 1, further comprising:
an excipient (a), a binder (b), a disintegrant (c) and a lubricant (d),
wherein the excipient (a) is at least one member selected from the group consisting of sugars, sugar alcohols, starches, and celluloses;
the binder (b) is a cellulose derivative;
the disintegrant (c) is at least one member selected from the group consisting of cellulose derivatives and starch derivatives; and
the lubricant (d) is a stearate.

Item 3. The tablet according to Item 2,
wherein the excipient (a) is at least one member selected from the group consisting of lactose, corn starch, and microcrystalline cellulose;
the binder (b) is hydroxypropyl cellulose;
the disintegrant (c) is at least one member selected from the group consisting of low-substituted hydroxypropyl cellulose, croscarmellose sodium, and sodium carboxymethyl starch; and
the lubricant (d) is magnesium stearate.

Item 4. The tablet according to Item 2 or 3, wherein the tablet is an uncoated tablet comprising:
0.05 to 25% by weight of 7-[4-(4-benzo[b]thiophen-4-yl-piperazin-1-yl)butoxy]-1H-quinolin-2-one or a salt thereof;
10 to 98.5% by weight of the excipient (a);
0.1 to 20% by weight of the binder (b);
1 to 25% by weight of the disintegrant (c); and
0.1 to 10% by weight of the lubricant (d), with respect to the weight of the uncoated tablet.

Item 5. The tablet according to any one of Items 2 to 4, wherein per 1 part by weight of 7-[4-(4-benzo[b]thiophen-4-yl-piperazin-1-yl)butoxy]-1H-quinolin-2-one or a salt thereof, the tablet comprises:
1 to 2000 parts by weight of the excipient (a);
0.01 to 100 parts by weight of the binder (b);
0.1 to 500 parts by weight of the disintegrant (c); and
0.01 to 50 parts by weight of the lubricant (d).

Item 6. The tablet according to any one of Items 1 to 5, which further comprises a coating layer on the surface thereof.

Item 7. The tablet according to Item 6, which further comprises the colorant (e) in the coating layer,
wherein the colorant (e) contains an iron oxide, and
the tablet contains 0.1 to 50% by weight of the colorant (e) with respect to the weight of the coating layer.

Item 8. The tablet according to any one of Items 1 to 7, which is obtained by forming, into a tablet, a granulated substance obtained through wet granulation.

Item 9. The tablet according to any one of Items 1 to 8, wherein the tablet does not contain povidone or crospovidone.

Item 10. A method for producing a tablet, the method comprising the steps of:
(1) granulating a mixture containing 7-[4-(4-benzo[b]thiophen-4-yl-piperazin-1-yl)butoxy]-1H-quinolin-2-one or a salt thereof, an excipient (a), a binder (b), and a disintegrant (c), and further mixing thereto a lubricant (d); and
(2) forming the obtained mixture into a tablet,
wherein the excipient is at least one member selected from the group consisting of sugars, sugar alcohols, starches, and celluloses;
the binder (b) is a cellulose derivative;
the disintegrant (c) is at least one member selected from the group consisting of cellulose derivatives and starch derivatives; and
the lubricant (d) is a stearate.

Item 11. The method for producing the tablet according to Item 10, further comprising the step of:

(3) mixing a coating agent, a colorant (e), and a liquid medium to obtain a mixture, and coating the surface of the tablet using the mixture.

Advantageous Effects of Invention

The tablet of the present invention exhibits excellent disintegration ability, storage stability, and high photostability, so that it can be effectively used in the medical field.

BRIEF DESCRIPTION OF DRAWINGS

FIG. 1 is a graph showing dissolution test results of tablets obtained in Examples 1-1 to 1-3, and Examples 2-1 to 2-3.

DESCRIPTION OF EMBODIMENTS

The tablet of the present invention comprises Compound (I) or a salt thereof as an active ingredient.

Here, the tablet of the present invention may be an uncoated tablet having no coating layer applied thereon or a coated tablet having a coating layer on the surface thereof. Furthermore, the tablet of the present invention may be used as an orally disintegrating tablet.

Compound (I) or a salt thereof can be produced by a known method, for example, that disclosed in Japanese Unexamined Patent Publication No. 2006-316052 or a method based thereon.

Salts of Compound (I) are not particularly limited as long as they are pharmacologically acceptable. Preferable examples thereof include: metal salts such as alkali metal salts (e.g., sodium salts and potassium salts), alkaline earth metal salts (e.g., calcium salts and magnesium salts), salts of inorganic bases such as ammonium salts, alkali metal carbonates (e.g., lithium carbonate, potassium carbonate, sodium carbonate, and cesium carbonate), alkali metal hydrogen carbonates (e.g., lithium hydrogen carbonate, sodium hydrogen carbonate, and potassium hydrogen carbonate), and alkali metal hydroxides (e.g., lithium hydroxide, sodium hydroxide, potassium hydroxide, and cesium hydroxide); salts of organic bases such as tri(lower)alkylamines (e.g., trimethylamine, triethylamine, and N-ethyldiisopropylamine), pyridine, quinoline, piperidine, imidazole, picoline, dimethylaminopyridine, dimethylaniline, N-(lower)alkyl-morpholine (e.g., N-methylmorpholine), 1,5-diazabicyclo[4.3.0]non-5-ene (DBN), 1,8-diazabicyclo[5.4.0]undec-7-ene (DBU), 1,4-diazabicyclo[2.2.2]octane (DABCO); salts of inorganic acids such as hydrochloride, hydrobromate, sulfate, nitrate, and phosphate; salts of organic acids such as formate, acetate, propionate, oxalate, malonate, succinate, fumarate, maleate, lactate, malate, citrate, tartrate, carbonate, picrate, methanesulfonate, ethanesulfonate, p-toluenesulfonate, and glutamate; and the like.

Compound (I) or a salt thereof in the above forms may be used singly or in a combination of two or more.

The content of Compound (I) or a salt thereof is preferably about 0.05 to 25% by weight, and more preferably about 0.1 to 15% by weight with respect to the weight of the tablet (the weight of an uncoated tablet before applying a coating when the tablet is a coated tablet).

The tablet of the present invention preferably comprises additives such as an excipient (a), a binder (b), a disintegrant (c), and a lubricant (d).

Examples of excipients (a) include, for example, sugar such as fructose, white soft sugar, sucrose, powdered sucrose, lactose, powdered hydrogenated maltose starch syrup, and maltose; sugar alcohols such as D-mannitol, D-sorbitol, xylitol, erythritol, maltitol; starch such as wheat starch, corn starch, and potato starch; starch derivatives such as dextrin, beta-cyclodextrin; cellulose or ca derivative thereof such as microcrystalline cellulose, powdered cellulose, ethyl cellulose, carboxymethyl cellulose (carmellose), sodium carboxymethyl cellulose (carmellose sodium), and microcrystalline cellulose/carmellose sodium; silicic acid or a salt thereof such as light anhydrous silicic acid, hydrated silicon dioxide, silicon dioxide, calcium silicate, magnesium silicate, and magnesium aluminometasilicate; kaolin; titanium oxide; magnesium oxide; talc; precipitated calcium carbonate; anhydrous dibasic calcium phosphate.

These excipients (a) may be used singly or in a combination of two or more. Among these, sugar, a sugar alcohol, starch, and cellulose are preferable, and lactose, microcrystalline cellulose and corn starch are more preferable.

The excipient (a) content is not particularly limited, and is preferably about 10 to 98.5% by weight with respect to the weight of the tablet (when the tablet is coated, the weight of the uncoated tablet), more preferably about 20 to 95%, and still more preferably about 30 to 90% by weight.

The excipient (a) amount is not particularly limited, and is preferably about 1 to 2000 parts by weight per 1 part by weight of Compound (I) or a salt thereof, and more preferably about 3 to 1800 parts by weight.

By setting the content and the amount of the excipient (a) as described above, the productivity can be improved.

Examples of the binder (b) include sucrose; white soft sugar; pregelatinized starch; partially pregelatinized starch; cellulose or a derivative thereof such as microcrystalline cellulose, methyl cellulose, ethyl cellulose, sodium carboxymethyl cellulose (carmellose sodium), hydroxyethyl cellulose, hydroxyethyl methyl cellulose, hydroxypropyl cellulose, low-substituted hydroxypropyl cellulose, hydroxypropyl methyl cellulose (hypromelloses such as hypromellose 2208, hypromellose 2906, and hypromellose 2910), other polysaccharides such as acacia, powdered acacia, agar, powdered agar, guar gum, tragacanth, powdered tragacanth, pullulan, and pectin; acrylic acid based polymer such as methacrylic acid copolymer L, methacrylic acid copolymer LD, methacrylic acid copolymer S, ethyl acrylate-methyl methacrylate copolymer dispersion, aminoalkyl methacrylate copolymer E, and aminoalkyl methacrylate copolymer RS; sodium alginate; purified gelatin; hydrolyzed gelatin powder; carboxyvinyl polymer; copolyvidone; povidone; polyvinyl alcohol. These binders (b) may be used singly or in a combination of two or more. Among these, a cellulose derivative is preferable, and hydroxypropyl cellulose is more preferable. It should be noted that, when povidone is contained as a binder (b), the obtained tablet tends to have reduced photostability and storage stability. Therefore, it is more preferable if this component is substantially not contained.

The binder (b) content is not particularly limited, and is preferably about 0.1 to 20% by weight with respect to the weight of the tablet (when the tablet is coated, the weight of the uncoated tablet), and more preferably about 0.5 to 5% by weight.

The binder (b) amount is not particularly limited, and is preferably about 0.01 to 100 parts by weight per 1 part by weight of Compound (I) or a salt thereof, and more preferably about 0.1 to 50 parts by weight. By setting the content and amount of the binder (b) as described above, the productivity and disintegration ability can be improved.

Examples of disintegrants (c) include starch or a derivative thereof such as wheat starch, corn starch, potato starch, partially pregelatinized starch, sodium carboxymethyl starch, and hydroxypropyl starch; cellulose or a derivative thereof such as microcrystalline cellulose, carboxymethyl cellulose (carmellose), calcium carboxymethyl cellulose (carmellose calcium), croscarmellose sodium, and low-substituted hydroxypropyl cellulose; crospovidone; alginic acid; and bentonite. These disintegrants (c) may be used singly or in a combination of two or more. Among these, starch or a derivative thereof, and cellulose or a derivative thereof are preferable, and sodium carboxymethyl starch, carmellose calcium, croscarmellose sodium and low-substituted hydroxypropyl cellulose are more preferable. It should be noted that, when crospovidone is contained, the obtained tablet tends to have reduced photostability and storage stability. Therefore, it is more preferable if this component is substantially not contained.

Here, in the present specification, "low-substituted hydroxypropyl cellulose" is a derivative of cellulose including hydroxypropoxyl groups by about 5 to 16%. The amount of the hydroxypropoxyl groups in the low-substituted hydroxypropyl cellulose may be measured by a method listed in, for example, the Japanese Pharmacopeia. The low-substituted hydroxypropyl cellulose may be produced by a method known in the art, or a commercially available product thereof may also be used. Examples of commercially available products of the low-substituted hydroxypropyl cellulose include, but are not limited to, "LH series" and "NBD series" manufactured by Shin-Etsu Chemical Co., Ltd.

Furthermore, in the present specification, "hydroxypropyl cellulose" is a derivative of cellulose including hydroxypropoxyl groups by about 50 to 85%. The amount of the hydroxypropoxyl groups in the hydroxypropyl cellulose may be measured by a method listed in, for example, the Japanese Pharmacopeia. The hydroxypropyl cellulose may be produced by a method known in the art, or a commercially available product thereof may also be used. Examples of commercially available products of the hydroxypropyl cellulose include, but are not limited to, "HPC series" manufactured by Nippon Soda Co., Ltd.; and "Klucel series" manufactured by Hercules Inc.

In the present specification, "sodium carboxymethyl starch" is a derivative of starch including sodium about 6 to 11%.

The disintegrant (c) content is not particularly limited, and is preferably about 1 to 25% by weight with respect to the weight of the tablet (when the tablet is coated, the weight of the uncoated tablet), more preferably about 2 to 20% by weight, and still more preferably about 3 to 15% by weight.

Furthermore, the disintegrant (c) amount is not particularly limited, and is preferably about 0.1 to 500 parts by weight per 1 part by weight of Compound (I) or a salt thereof, more preferably about 1 to 500 parts by weight, and still more preferably about 1 to 250 parts h weight. By setting the content and amount of the disintegrant (c) as described above, the disintegration ability can be improved.

Examples of lubricants (d) include stearic acid or a salt thereof such as stearic acid, aluminum stearate, calcium stearate, and magnesium stearate; carnauba wax; glycerol ester of fatty acid; hydrogenated oil; yellow beeswax; white beeswax; talc; sodium stearyl fumarate; and polyethylene glycol (macrogols such as macrogol 400, macrogol 600, macrogol 1500, macrogol 4000, and macrogol 6000). These lubricants (d) may be used singly or in a combination of two or more. Among these, stearate, sucrose ester of fatty acid, and hydrogenated oil are preferable, and magnesium stearate is more preferable.

The lubricant (d) content is not particularly limited, and is preferably about 0.1 to 10% by weight with respect to the weight of the tablet (when the tablet is coated, the weight of the uncoated tablet), more preferably about 0.2 to 8% by weight, and still more preferably about 0.3 to 7% by weight.

The lubricant (d) amount is not particularly limited, and is preferably about 0.01 to 50 parts by weight per 1 part by weight of Compound (I) or a salt thereof, and more preferably about 0.02 to 30 parts by weight. By setting the content and amount of the lubricant (d) as described above, the tabletability can be improved.

The tablet of the present invention may comprise other components in addition to the excipient (a), the binder (b), the disintegrant (c), and the lubricant (d). Examples of other components include various additives applicable to tablets, such as colorants, pH adjusters, preservatives, absorbefacients, taste enhancers, antioxidants, buffers, chelating agents, abrasives, solvents, hardening agents, surfactants, sweeteners, fluidizers, brightening agents, and flavors. Those components may be used in an amount that does not adversely affect the present invention.

The tablet of the present invention may be used as an uncoated tablet that comprises the above described components but does not have a coating layer provided thereon. A coated tablet (film-coated tablet) provided with a coating layer is preferable to achieve long-term storage stability and prevent degradation due to light or the like.

The coating layer may comprise pharmaceutical additives, such as a coating agent, plasticizer, dispersant, defoaming agent, and the like, usually used for coating (for providing a coat to) orally administrable pharmaceutical preparations.

Examples of additives include celluloses such as microcrystalline cellulose, methyl cellulose, ethyl cellulose, carmellose sodium, hydroxypropyl cellulose, and hydroxypropyl methyl cellulose (hypromellose) and derivatives thereof; polyethylene glycol (macrogol); polyvinyl alcohol; titanium oxide; and talc. These additives may be used singly or in a combination of two or more.

Among these, a combination of hydroxypropyl methyl cellulose (hypromellose), talc, and titanium oxide, which are components for coating agent, is preferable. It should be noted that, when polyethylene glycol (macrogol) exists in the coating layer, the obtained tablet tends to have reduced photostability and storage stability. Therefore, it is more preferable if polyethylene glycol (macrogol) is substantially not contained.

Furthermore, with regard to the coated tablet, by coloring the coating layer, photostability can be supplied to the coated tablet. Therefore, a colorant (e) is preferably added to the coating agent for coating the tablet.

Examples of colorants (e) include: iron oxides such as red ferric oxide, yellow ferric oxide, and black iron oxide; titanium oxide; beta-carotene; food blue No. 2; food blue No. 2 aluminium lake; and riboflavin.

Among these, containing an iron oxide is more preferable from a standpoint of not only adding a color to the tablet but also further improving photostability of the tablet.

The colorant (e) may be suitably selected, or used in combination, depending on the color of the coated tablet prepared. For example, to obtain a white coated tablet, titanium oxide is used; to obtain a red coated tablet, a combination of titanium oxide and red ferric oxide is used;

to obtain a yellow coated tablet, a combination of titanium oxide and yellow ferric oxide is used; to obtain a blue coated tablet, a combination of titanium oxide and food blue No. 2 aluminium lake is used; to obtain an orange coated tablet, a combination of titanium oxide, red ferric oxide, and yellow ferric oxide is used; to obtain a green coated tablet, a combination of titanium oxide, yellow ferric oxide, and black iron oxide, or a combination of titanium oxide, yellow ferric oxide and food blue No. 2 aluminium lake is used; and to obtain a purple coated tablet, a combination of titanium oxide, red ferric oxide and black iron oxide, or a combination of titanium oxide, red ferric oxide and food blue No. 2 aluminium lake is used. As described above, a coated tablet may be made into various colors.

The colorant (e) content is preferably about 0.1 to 3% by weight with respect to the total weight of the coated tablet, and about 5 to 50% by weight with respect to the weight of the coating layer of the coated tablet.

The amount of a coating layer in tablet that is coated using the coating agent and a colorant (e) that is contained if necessary is preferably about 1 to 10 parts by weight per 100 parts by weight of a tablet (uncoated tablet) before having a coating provided thereon.

Specific preferable examples of the additives contained in the tablet of the present invention include:
  as an excipient (a), at least one member selected from the group consisting of sugars, sugar alcohols, starches, and celluloses;
  as a binder (b), cellulose derivatives;
  as a disintegrant (c), at least one member selected from the group consisting of cellulose derivatives and starch derivatives; and,
  as a lubricant (d), stearates.

From a standpoint of productivity and disintegration ability, these additives are preferably used in a combination of: as an excipient (a), at least one member selected from the group consisting of lactose, corn starch, and microcrystalline cellulose; as a binder (b), hydroxypropyl cellulose; as a disintegrant (c), at least one member selected from the group consisting of low-substituted hydroxypropyl cellulose, croscarmellose sodium, and sodium carboxymethyl starch; and, as a lubricant (d), magnesium stearate.

The tablet of the present invention preferably contains each of the components in the content and amount shown below.

Content of each of the Components in the Tablet Compound (I) or a salt thereof:
  0.05 to 20% by weight
  Sugar and/or sugar alcohol: 20 to 80% by weight
  Starch: 5 to 50% by weight
  Cellulose: 1 to 30% by weight
  Hydroxypropyl cellulose: 0.1 to 20% by weight
  At least one member selected from the group consisting of low-substituted hydroxypropyl cellulose, croscarmellose sodium, and starch derivatives:
  1 to 25% by weight
  Stearate 0.1 to 10% by weight
  Amount of each of the Components in the Tablet per 1 part by weight of Compound (I) or a Salt thereof
  Sugar and/or sugar alcohol: 1 to 1000 parts by weight
  Starch: 1 to 400 parts by weight
  Cellulose: 0.1 to 200 parts by weight
  Hydroxypropyl cellulose: 0.01 to 100 parts by weight
  At least one member selected from the group consisting of low-substituted hydroxypropyl cellulose, croscarmellose sodium, and starch derivatives:
  0.1 to 500 parts by weight
  Stearate: 0.01 to 50 parts by weight The content and amount of each of the components in a further preferable mode of the tablet of the present invention are shown below.

Content of each of the Components in the Tablet Compound (I) or a salt thereof:
  0.1 to 15% by weight
  Lactose: 30 to 60% by weight
  Corn starch: 10 to 30% by weight
  Microcrystalline cellulose: 5 to 20% by weight
  Hydroxypropyl cellulose: 0.5 to 10% by weight
  At least one member selected from the group consisting of low-substituted hydroxypropyl cellulose, croscarmellose sodium, and sodium carboxymethyl starch:
  2 to 15% by weight
  Magnesium stearate: 0.1 to 10% by weight
  Amount of each of the Components in the Tablet per 1 Part by Weight of Compound (I) or a Salt Thereof
  Lactose: 2 to 500 parts by weight
  Corn starch: 2 to 200 parts by weight
  Microcrystalline cellulose: 0.5 to 100 parts by weight
  Hydroxypropyl cellulose: 0.05 to 50 parts by weight
  At least one member selected from the group consisting of low-substituted hydroxypropyl cellulose, croscarmellose sodium, and sodium carboxymethyl starch:
  1 to 250 parts by weight
  Magnesium stearate: 0.05 to 30 parts by weight When the tablet of the present invention is a coated tablet, preferable examples of the additives contained in the coated tablet include, as the components for an uncoated tablet before coating:
  as an excipient (a), at least one member selected from the group consisting of sugars, sugar alcohols, starches, and celluloses;
  as a binder (b), cellulose derivatives;
  as a disintegrant (c), at least one member selected from the group consisting of cellulose derivatives and starch derivatives; and
  as a lubricant (d), stearates, and
as components for the coating layer:
  cellulose derivatives, talc, titanium oxides and iron oxides as colorant (e).

Furthermore, when the tablet of the present invention is a coated tablet, a more preferable combination is a formulation obtained by applying a coating layer on an uncoated tablet; in which, the uncoated tablet contains Compound (I) or a salt thereof, lactose, corn starch, microcrystalline cellulose, low-substituted hydroxypropyl cellulose, hydroxypropyl cellulose, and magnesium stearate, and the coating layer contains hypromellose, talc, titanium oxide, and at least one colorant (e) (iron oxide) selected from the group consisting of red ferric oxide, yellow ferric oxide, and black iron oxide.

The preferable content and amount of each of the components, and further preferable content and amount of each of the components in a preferable mode of the coated tablet are shown below.

Content of each of the Components in the Uncoated Tablet
  Compound (I) or a salt thereof:
  0.05 to 20% by weight
  Sugar and/or sugar alcohol: 20 to 80% by weight
  Starch: 5 to 50% by weight
  Cellulose: 1 to 30% by weight
  Hydroxypropyl cellulose: 0.1 to 20% by weight At least one member selected from the group consisting of low-substituted hydroxypropyl cellulose, croscarmellose sodium, and starch derivatives:
1 to 25% by weight
Stearate: 0.1 to 10% by weight
Content of each of the Components in the Coating Layer (per entire coated tablet)
Cellulose derivative: 1 to 6% by weight
Talc: 0.1 to 1% by weight
Titanium oxide: 0.1 to 2% by weight
Iron oxide: 0.01 to 1% by weight
Amount of each of the Components in the Coated Tablet per 1 part by weight of Compound (I) or a Salt thereof
Lactose: 1 to 1000 parts by weight
Starch: 1 to 400 parts by weight
Cellulose: 0.1 to 200 parts by weight
Hydroxypropyl cellulose: 0.01 to 100 parts by weight
At least one member selected from the group consisting of low-substituted hydroxypropyl cellulose, croscarmellose sodium, and starch derivatives:
0.1 to 500 parts by weight
Stearate: 0.01 to 50 parts by weight
Hypromellose: 0.1 to 50 parts by weight
Talc: 0.01 to 10 parts by weight
Titanium oxide: 0.01 to 20 parts by weight
Iron oxide: 0.0005 to 5 parts by weight
The content and amount of each of the components in a further preferable mode of the coated tablet are shown below.
Content of each of the Components in the Uncoated Tablet
Compound (I) or a salt thereof:
0.1 to 15% by weight
Lactose: 30 to 60% by weight
Corn starch: 10 to 30% by weight
Microcrystalline cellulose: 5 to 20% by weight
Hydroxypropyl cellulose: 0.5 to 10% by weight
At least one member selected from the group consisting of low-substituted hydroxypropyl cellulose, croscarmellose sodium, and sodium carboxymethyl starch:
2 to 15% by weight
Magnesium stearate: 0.1 to 10% by weight
Content of each of the Components in the Coating Layer (per entire coated tablet)
Hypromellose: 1.5 to 4% by weight
Talc: 0.2 to 0.5% by weight
Titanium oxide: 0.2 to 1% by weight
Iron oxide: 0.02 to 0.5% by weight
Amount of each of the Components in the Coated Tablet per 1 part by weight of Compound (I) or a Salt thereof
Lactose: 2 to 500 parts by weight
Corn starch: 2 to 200 parts by weight
Microcrystalline cellulose: 0.5 to 100 parts by weight
Hydroxypropyl cellulose: 0.05 to 50 parts by weight
At least one member selected from the group consisting of low-substituted hydroxypropyl cellulose, croscarmellose sodium, and sodium carboxymethyl starch:
1 to 250 parts by weight
Magnesium stearate: 0.05 to 30 parts by weight
Hypromellose: 0.2 to 40 parts by weight
Talc: 0.02 to 8 parts by weight
Titanium oxide: 0.02 to 15 parts by weight
Iron oxide: 0.001 to 2.5 parts by weight The method for producing the tablet of the present invention is not particularly limited; for example, the tablet of the present invention can be produced by a step of forming into a tablet a mixture containing Compound (I) or a salt thereof, and components other than Compound (I) or a salt thereof necessary to form a tablet (i.e., an excipient (a), a binder (b), a disintegrant (c), a lubricant (d) and the like). Alternatively, the tablet of the present invention can be produced by the method comprising: granulating a mixture containing Compound (I) or a salt thereof, an excipient (a), a binder (b), and a disintegrant (c), and further mixing thereto a lubricant (d); and forming the obtained mixture into a tablet.

The granulation method used for forming the granulated substance into a tablet is not particularly limited. Examples thereof include dry granulation methods and wet granulation methods (e.g., a fluidized-bed granulation method, and a knead-granulation method). Among these, wet granulation methods are preferably used for the production, from a standpoint of being able to uniformly mix the active ingredient and other components in the tablet, and being able to obtain a tablet whose components are uniformly distributed therein.

Examples of the tablet forming methods include tableting, such as direct compression tableting, dry tableting, wet tableting, and external lubrication tableting.

The coated tablet of the present invention can be produced by mixing a coating agent, a colorant (e), and a liquid medium; spraying the obtained liquid mixture on the surface of the uncoated tablet obtained by the method described above; and successively drying it.

Examples of the liquid medium (e.g., a dispersion medium) used in the above described step include: water; methanol, ethanol, isopropanol, and like lower alcohols; acetone, methyl ethyl ketone, and like ketones; dichloromethane, dichloromethane, chloroform, carbon tetrachloride and like halogenated hydrocarbons; and mixtures of these solvents.

The tablet of the present invention preferably comprises Compound (I), which is an active ingredient, or a salt thereof in an amount of about 0.05 to 25 mg calculated as Compound (I).

The dose of the tablet of the present invention is suitably selected according to the intended use; the patient's age, sex, and other conditions; the severity of the disease; and the like. The dose is preferably selected so that the amount of Compound (I) (i.e., the active ingredient) or a salt thereof taken is about 0.05 to 6 mg per day calculated as Compound (I).

EXAMPLES

The present invention is explained in detail below with reference to Examples. However, the scope of the present invention is not limited to these Examples. Note that in all of the Examples described below, Compound (I) was "7-[4-(4-benzo[b]thiophen-4-yl-piperazin-1-yl)butoxy]-1H-quinolin-2-one."

Example 1

Uncoated tablets (a tablet not provided with a coating layer) of Compound (I) were produced using the components and amounts shown in Table 1, by following the procedures described below.

Example 1-1

Compound (I), lactose, corn starch, microcrystalline cellulose (CEOLUS PH-301), and low-substituted hydroxypropylcellulose (LH-11, manufactured by Shin-Etsu Chemical Co., Ltd., hydroxypropoxyl groups content: 10.0 to 12.9%) were weighed and mixed. A separately prepared aqueous solution of hydroxypropylcellulose was added to the powder mixture, followed by wet kneading granulation. After drying and sizing the result, magnesium stearate was added thereto and mixed. The resulting mixture was compressed using a single tableting machine equipped with a punch of diameter 6.5 mm in such a manner that the weight of the tablet became 100 mg, obtaining uncoated tablets containing 10 mg of Compound (I) per tablet.

Example 1-2

Compound (I), lactose, corn starch, microcrystalline cellulose, and croscarmellose sodium were weighed and mixed. A separately prepared aqueous solution of hydroxypropylcellulose was added to the powder mixture, followed by wet kneading granulation. After drying and sizing the result, magnesium stearate was added thereto and mixed. The resulting mixture was compressed using a single tableting machine equipped with a punch of diameter 6.5 mm in such a manner that the weight of the tablet became 100 mg, obtaining uncoated tablets containing 10 mg of Compound (I) per tablet.

Example 1-3

Compound (I), lactose, corn starch, microcrystalline cellulose, and sodium carboxymethyl starch were weighed and mixed. A separately prepared aqueous solution of hydroxypropylcellulose was added to the powder mixture, followed by wet kneading granulation. After drying and sizing the result, magnesium stearate was added thereto and mixed. The resulting mixture was compressed using a single tableting machine equipped with a punch of diameter 6.5 mm in such a manner that the weight of the tablet became 100 mg, obtaining uncoated tablets containing 10 mg of Compound (I) per tablet.

TABLE 1

| Components (mg) | Example 1-1 | Example 1-2 | Example 1-3 |
|---|---|---|---|
| Compound (I) | 10.0 | 10.0 | 10.0 |
| Lactose | 48.2 | 53.2 | 53.2 |
| Corn starch | 20.0 | 20.0 | 20.0 |
| Microcrystalline cellulose | 10.0 | 10.0 | 10.0 |
| Low-substituted hydroxypropylcellulose | 10.0 | — | — |
| Croscarmellose sodium | — | 5.0 | — |
| Sodium carboxymethyl starch | — | — | 5.0 |
| Hydroxypropylcellulose | 1.0 | 1.0 | 1.0 |
| Magnesium stearate | 0.8 | 0.8 | 0.8 |
| Weight of uncoated tablet (mg) | 100.0 | 100.0 | 100.0 |

Table 2 shows the tablet properties of uncoated tablets obtained in Examples 1-1 to 1-3.

TABLE 2

| Tablet properties | Example 1-1 | Example 1-2 | Example 1-3 |
|---|---|---|---|
| Hardness (Kp, n = 3) | 5.4 | 5.6 | 4.7 |
| Thickness (mm, n = 3) | 2.78 | 2.77 | 2.82 |
| Disintegration time (mm:ss, n = 6) | 1:18-1:36 | 2:00-2:16 | 1:09-1:35 |

The measurement of disintegration time (disintegration test) results show the measurement results of six tablets of each Example. The test was performed using water as a test liquid according to the disintegration test of the Japanese Pharmacopeia (without an auxiliary disk).

Examples 2-1 to 2-3

The uncoated tablets produced in Examples 1-1 to 1-3 each having a weight of 100 mg and containing 10 mg of Compound (I) were subjected to coating by spraying a coating liquid comprising the coating layer components whose amounts are shown in Table 3 thereby obtaining coated tablets.

TABLE 3

| Components (mg) | Example 2-1 | Example 2-2 | Example 2-3 |
|---|---|---|---|
| Uncoated tablet | Example 1-1 | Example 1-2 | Example 1-3 |
| Weight of uncoated tablet (mg) | 100.0 | 100.0 | 100.0 |
| Coating layer (mg) | | | |
| Hypromellose | 2.07 | 2.07 | 2.07 |
| Macrogol 6000 | 0.30 | 0.30 | 0.30 |
| Talc | 0.30 | 0.30 | 0.30 |
| Titanium oxide | 0.30 | 0.30 | 0.30 |
| Yellow ferric oxide | 0.03 | 0.03 | 0.03 |
| Weight of coating layer (mg) | 3.0 | 3.0 | 3.0 |
| Weight of coated tablet (mg) | 103.0 | 103.0 | 103.0 |

Measurements of disintegration time (disintegration tests) were performed for the coated tablets produced in Examples 2-1 to 2-3 in the same manner as in Example 1-1. Table 4 shows the results. No delay in disintegration time due to coating was observed in the coated tablets produced in Examples 2-1 to 2-3.

TABLE 4

| | Example 2-1 | Example 2-2 | Example 2-3 |
|---|---|---|---|
| Disintegration time (mm:ss, n = 6) | 1:35-1:50 | 2:22-2:40 | 1:26-1:44 |

Dissolution tests were performed for the uncoated tablets produced in Examples 1-1 to 1-3, and the coated tablets produced in Examples 2-1 to 2-3. FIG. 1 shows the results.

The dissolution test results show the average values of the measurement results of two tablets of each Example. The dissolution test was performed in accordance with the dissolution test method (paddle method; 50 rpm) of the Japanese Pharmacopoeia, using a disodium hydrogenphosphate-citric acid buffer solution (900 mL) with pH 4.5 as a test liquid.

The dissolution test results confirm excellent dissolution profiles of the uncoated tablets produced in Examples 1-1 to 1-3 and the coated tablets produced in Examples 2-1 to 2-3.

Furthermore, a stability test was performed for the uncoated tablets produced in Examples 1-1 to 1-3 and the coated tablets produced in Examples 2-1 to 2-3 under the storage conditions of light irradiation (visible light: total illuminance of $1.8 \times 10^6$ lux·hr; ultraviolet light: total intensity of 300 W·hr/m$^2$) and a closed system at 40° C. (sealed in bottles for one month or three months). The contents of Compound (I) and impurity after the storage in each condition were measured. Table 5 shows the results.

Note that after the storage under the above light irradiation conditions, yellow coloring was observed in the uncoated tablets produced in Examples 1-1 to 1-3.

TABLE 5

| | Example No. | | | | | |
|---|---|---|---|---|---|---|
| | 1-1 | 1-2 | 1-3 | 2-1 | 2-2 | 2-3 |
| Contents of Compound (I) (%, n = 3) | | | | | | |
| Initial | 98.1 | 99.4 | 99.7 | 99.6 | 101.5 | 101.9 |
| Light irradiation | 98.3 | 99.3 | 99.8 | 100.0 | 101.7 | 102.3 |
| 40° C. - 1 month | 99.6 | 101.4 | 100.8 | 102.2 | 103.5 | 103.4 |
| 40° C. - 3 months | 98.0 | 100.5 | 100.0 | 100.1 | 102.8 | 103.5 |
| Content of impurity (%, n = 1) | | | | | | |
| Initial | 0.365 | 0.362 | 0.371 | 0.373 | 0.367 | 0.374 |
| Light irradiation | 0.662 | 0.634 | 0.592 | 0.477 | 0.500 | 0.463 |
| 40° C. - 1 month | 0.354 | 0.78 | 0.376 | 0.370 | 0.393 | 0.411 |
| 40° C. - 3 months | 0.409 | 0.373 | 0.401 | 0.385 | 0.409 | 0.419 |

Example 3-1

Using the components and amounts shown in Table 6, uncoated tablets containing 0.25 mg of Compound (I) per tablet were produced in the same manner as in Example 1-1, except that a rotary tableting machine equipped with a punch of diameter 6.0 mm was used to obtain uncoated tablets each having a weight of 90 mg.

TABLE 6

| Components (mg) | Example 3-1 |
|---|---|
| Compound (I) | 0.25 |
| Lactose | 48.15 |
| Corn starch | 20.0 |
| Microcrystalline cellulose | 10.0 |
| Low-substituted hydroxypropylcellulose | 10.0 |
| Hydroxypropylcellulose | 1.0 |
| Magnesium stearate | 0.6 |
| Weight of uncoated tablet (mg) | 90.0 |

Examples 3-2 to 3-9

The uncoated tablets produced in Example 3-1 each having a weight of 90 mg and containing 0.25 mg of Compound (I) were subjected to coating by spraying a coating liquid comprising the coating layer components whose amounts are shown in Table 7 thereby obtaining coated tablets.

TABLE 7

| | Example No. | | | | | | | |
|---|---|---|---|---|---|---|---|---|
| | 3-2 | 3-3 | 3-4 | 3-5 | 3-6 | 3-7 | 3-8 | 3-9 |
| Uncoated tablet Weight of uncoated tablet (mg) | Example 3-1 90.0 | | | | | | | |
| Coating layer (mg) | | | | | | | | |
| Hypromellose | 1.8 | 2.1 | 1.8 | 2.1 | 1.8 | 2.1 | 1.8 | 2.1 |
| Macrogol 6000 | 0.3 | — | 0.3 | — | 0.3 | — | 0.3 | — |
| Talc | 0.3 | 0.3 | 0.3 | 0.3 | 0.3 | 0.3 | 0.3 | 0.3 |
| Titanium oxide | 0.6 | 0.6 | 0.54 | 0.54 | 0.54 | 0.54 | 0.54 | 0.54 |
| red ferric oxide | — | — | 0.06 | 0.06 | — | — | — | — |
| Yellow ferric pride | — | — | — | — | 0.06 | 0.06 | — | — |
| Food blue No. 2 Aluminum lake (3-5%) | — | — | — | — | — | — | 0.06 | 0.06 |
| Weight of coat layer (mg) | 3.0 | 3.0 | 3.0 | 3.0 | 3.0 | 3.0 | 3.0 | 3.0 |
| Weight of coated tablet (mg) | 93.0 | 93.0 | 93.0 | 93.0 | 93.0 | 93.0 | 93.0 | 93.0 |

Furthermore, a stability test was performed for the uncoated tablets produced in Example 3-1 and the coated tablets produced in Examples 3-2 to 3-9 under the storage conditions of light irradiation (visible light: total illuminance of $1.8 \times 10^6$ lux·hr; ultraviolet light: total intensity of 300 W·hr/m$^2$) and an open system at 40° C./75% RH (three months, six months), i.e., conditions as or more severe as those of Examples 1-1 to 1-3 and Examples 2-1 to 2-3. The contents of impurity after the storage in each condition were measured. Table 8 shows the results.

No increase in impurity was observed in the tablets of Examples 3-5 and 3-7, even after the light irradiation.

| | Example No. | | | | | | | | |
|---|---|---|---|---|---|---|---|---|---|
| | 3-1 | 3-2 | 3-3 | 3-4 | 3-5 | 3-6 | 3-7 | 3-8 | 3-9 |
| | (Content of Impurity: %, n = 1) | | | | | | | | |
| Initial | 0.687 | 0.772 | 0.773 | 0.683 | 0.713 | 0.677 | 0.805 | 0.951 | 0.909 |
| Light irradiation | 4.142 | 2.069 | 1.469 | 1.401 | 0.676 | 1.493 | 0.675 | 2.573 | 1.186 |
| 40° C./75% RH - 3 months | 0.980 | 1.820 | 0.900 | 1.613 | 1.093 | 1.483 | 1.112 | 2.055 | 1.393 |
| 40° C./75% RH - 6 months | 1.140 | 2.264 | 1.672 | 2.232 | 1.232 | 1.766 | 1.247 | 2.130 | 1.783 |

Examples 4-1 to 4-13

Coated tablets of Compound (I) of Examples 4-1 to 4-13 that comprise the components and amounts shown in Table 9 were produced in the same manner as in Example 3-2.

TABLE 9

| | Example No. | | | | | | | | | | | | |
|---|---|---|---|---|---|---|---|---|---|---|---|---|---|
| Components (mg) | 4-1 | 4-2 | 4-3 | 4-4 | 4-5 | 4-6 | 4-7 | 4-8 | 4-9 | 4-10 | 4-11 | 4-12 | 4-13 |
| Compound (I) | 0.05 | 0.25 | 0.5 | 1.0 | 2.0 | 3.0 | 4.0 | 5.0 | 6.0 | 0.25 | 0.25 | 0.25 | 1.0 |
| Lactose | 46.35 | 48.15 | 47.9 | 47.4 | 46.4 | 45.4 | 44.4 | 43.4 | 42.4 | 48.15 | 48.15 | 48.15 | 47.4 |
| Corn starch | 20.0 | 20.0 | 20.0 | 20.0 | 20.0 | 20.0 | 20.0 | 20.0 | 20.0 | 20.0 | 20.0 | 20.0 | 20.0 |

TABLE 9-continued

| Components (mg) | 4-1 | 4-2 | 4-3 | 4-4 | 4-5 | 4-6 | 4-7 | 4-8 | 4-9 | 4-10 | 4-11 | 4-12 | 4-13 |
|---|---|---|---|---|---|---|---|---|---|---|---|---|---|
| Microcrystalline cellulose | 10.0 | 10.0 | 10.0 | 10.0 | 10.0 | 10.0 | 10.0 | 10.0 | 10.0 | 10.0 | 10.0 | 10.0 | 10.0 |
| Low-substituted hydroxypropylcellulose | 10.0 | 10.0 | 10.0 | 10.0 | 10.0 | 10.0 | 10.0 | 10.0 | 10.0 | 10.0 | 10.0 | 10.0 | 10.0 |
| Hydroxypropylcellulose | 1.0 | 1.0 | 1.0 | 1.0 | 1.0 | 1.0 | 1.0 | 1.0 | 1.0 | 1.0 | 1.0 | 1.0 | 1.0 |
| Magnesium stearate | 0.6 | 0.6 | 0.6 | 0.6 | 0.6 | 0.6 | 0.6 | 0.6 | 0.6 | 0.6 | 0.6 | 0.6 | 0.6 |
| Weight of uncoated | 90.0 | 90.0 | 90.0 | 90.0 | 90.0 | 90.0 | 90.0 | 90.0 | 90.0 | 90.0 | 90.0 | 90.0 | 90.0 |
| Hypromellose | 2.1 | 2.1 | 2.1 | 2.1 | 2.1 | 2.1 | 2.1 | 2.1 | 2.1 | 2.1 | 2.1 | 2.1 | 2.1 |
| Talc | 0.3 | 0.3 | 0.3 | 0.3 | 0.3 | 0.3 | 0.3 | 0.3 | 0.3 | 0.3 | 0.3 | 0.3 | 0.3 |
| Titanium oxide | 0.54 | 0.54 | 0.54 | 0.54 | 0.54 | 0.54 | 0.54 | 0.54 | 0.54 | 0.54 | 0.54 | 0.54 | 0.57 |
| Red ferric oxide | 0.06 | 0.06 | 0.06 | 0.06 | 0.06 | 0.06 | 0.06 | 0.06 | 0.06 | — | — | 0.02 | 0.01 |
| Yellow ferric oxide | — | — | — | — | — | — | — | — | — | — | 0.04 | — | — |
| Weight of coating layer (mg) | 3.0 | 3.0 | 3.0 | 3.0 | 3.0 | 3.0 | 3.0 | 3.0 | 3.0 | 3.0 | 3.0 | 3.0 | 3.0 |
| Weight of coated tablet (mg) | 93.0 | 93.0 | 93.0 | 93.0 | 93.0 | 93.0 | 93.0 | 93.0 | 93.0 | 93.0 | 93.0 | 93.0 | 93.0 |

INDUSTRIAL APPLICABILITY

The tablet of the present invention comprising benzothiophen compound (I) or a salt thereof has excellent disintegration ability, storage stability, and photostability. Therefore, the tablet of the present invention is highly usable in the medical field.

The invention claimed is:

1. A tablet comprising 7-[4-(4-benzo[b]thiophen-4-yl-piperazin-1-yl)butoxy]-1H-quinolin-2-one or a salt thereof as an active ingredient, an excipient (a), a binder (b), a disintegrant (c), a lubricant (d), and a coating, wherein the uncoated tablet comprises:
    0.05 to 25% by weight of 7-[4-(4-benzo[b]thiophen-4-yl-piperazin-1-yl)butoxy]-1H-quinolin-2-one or a salt thereof,
    10 to 98.5% by weight of the excipient (a), which is at least one member selected from the group consisting of lactose, corn starch, and microcrystalline cellulose;
    0.1 to 20% by weight of the binder (b), which is hydroxypropyl cellulose;
    1 to 25% by weight of the disintegrant (c), which is at least one member selected from the group consisting of low-substituted hydroxypropyl cellulose, croscarmellose sodium, and sodium carboxymethyl starch; and
    0.1 to 10% by weight of the lubricant (d), which is magnesium stearate;
    wherein said coating comprises hydroxypropyl methylcellulose, talc, and a colorant (e), the colorant (e) is present in an amount ranging from 0.1 to 50% by weight of the coating and comprises iron oxide and titanium oxide, and the coating substantially does not contain polyethylene glycol.

2. The tablet according to claim 1, wherein per 1 part by weight of 7-[4-(4-benzo[b]thiophen-4-yl-piperazin-1-yl)butoxy]-1H-quinolin-2-one or a salt thereof, the tablet comprises:
    1 to 2000 parts by weight of the excipient (a);
    0.01 to 100 parts by weight of the binder (b);
    0.1 to 500 parts by weight of the disintegrant (c); and
    0.01 to 50 parts by weight of the lubricant (d).

3. The tablet according to claim 1, which is obtained by forming, into a tablet, a granulated substance obtained through wet granulation.

4. The tablet according to claim 1, wherein the tablet does not contain povidone or crospovidone.

5. The tablet according to claim 1, wherein the excipient (a) is lactose, corn starch, and microcrystalline cellulose; and the disintegrant (c) is low-substituted hydroxypropyl cellulose.

6. A method for producing a tablet, the method comprising the steps of:
    (1) granulating a mixture containing 7-[4-(4-benzo[b]thiophen-4-yl-piperazin-1-yl)butoxy]-1H-quinolin-2-one or a salt thereof, an excipient (a), a binder (b), and a disintegrant (c), and further mixing thereto a lubricant (d); and
    (2) forming the obtained mixture into a tablet form; and
    (3) mixing a coating agent, a colorant (e), and a liquid medium to obtain a coating mixture, and coating the surface of the tablet form using the coating mixture to form the tablet,
    wherein the tablet comprises:
        0.05 to 25% by weight of 7-[4-(4-benzo[b]thiophen-4-yl-piperazin-1-yl)butoxy]-1H-quinolin-2-one or a salt thereof,
        10 to 98.5% by weight of the excipient (a), which is at least one member selected from the group consisting of lactose, corn starch, and microcrystalline cellulose;
        0.1 to 20% by weight of the binder (b), which is hydroxypropyl cellulose;
        1 to 25% by weight of the disintegrant (c), which is at least one member selected from the group consisting of low-substituted hydroxypropyl cellulose, croscarmellose sodium, and sodium carboxymethyl starch; and
        0.1 to 10% by weight of the lubricant (d), which is magnesium stearate;
    the tablet further comprising a coating layer on the surface thereof,
        wherein said coating agent comprises hydroxypropyl methyl cellulose and talc, the colorant (e) is present in an amount ranging from 0.1 to 50% by weight of the coating mixture and comprises iron oxide and titanium oxide, and
        the coating mixture substantially does not contain polyethylene glycol.

7. The method for producing the tablet according to claim 6, wherein the excipient (a) is lactose, corn starch, and microcrystalline cellulose; and the disintegrant (c) is low-substituted hydroxypropyl cellulose.

* * * * *

UNITED STATES PATENT AND TRADEMARK OFFICE
CERTIFICATE OF CORRECTION

PATENT NO. : 10,307,419 B2  
APPLICATION NO. : 15/713427  
DATED : June 4, 2019  
INVENTOR(S) : Yoshiharu Inoue Page 1 of 1

It is certified that error appears in the above-identified patent and that said Letters Patent is hereby corrected as shown below:

In the Claims

In Claim 1, before Line 49 before the phrase "wherein said coating comprises hydroxypropyl methyl-", please add the phrase "the tablet further comprising a coating layer on the surface thereof,".

Signed and Sealed this  
Twenty-second Day of October, 2019

Andrei Iancu  
*Director of the United States Patent and Trademark Office*